United States Patent [19]
Bronson

[11] Patent Number: 5,389,519
[45] Date of Patent: * Feb. 14, 1995

[54] METHOD OF SCREENING FOR INFERTILITY

[75] Inventor: Richard A. Bronson, Huntington, N.Y.

[73] Assignee: The Research Foundation of the State University of New York, Albany, N.Y.

[ * ] Notice: The portion of the term of this patent subsequent to Oct. 26, 2010 has been disclaimed.

[21] Appl. No.: 857,165

[22] Filed: Mar. 25, 1992

Related U.S. Application Data

[63] Continuation-in-part of Ser. No. 740,042, Aug. 1, 1991, Pat. No. 5,256,539.

[51] Int. Cl.⁶ .................... E01N 33/567; E01N 33/53
[52] U.S. Cl. ...................... 435/7.21; 435/7.1; 435/7.2; 435/806; 435/29; 436/63; 436/906
[58] Field of Search .............. 435/29, 7.1, 7.2, 7.21, 435/2, 806; 436/63, 906

[56] References Cited

U.S. PATENT DOCUMENTS

| | | | |
|---|---|---|---|
| 3,660,558 | 5/1972 | Ericsson | 435/2 |
| 4,683,213 | 7/1987 | Ax | 436/501 |
| 4,767,703 | 8/1988 | Ax et al. | 435/29 |
| 4,789,734 | 12/1988 | Pierschbacher | 530/395 |
| 4,894,326 | 1/1990 | Matsuura | 435/7.21 |
| 4,894,328 | 1/1990 | Alderete et al. | 435/7.36 |
| 4,980,279 | 12/1990 | Peters et al. | 435/7.92 |
| 4,999,283 | 3/1991 | Zavos et al. | 435/2 |
| 5,256,539 | 10/1993 | Bronson | 435/7.21 |

OTHER PUBLICATIONS

Bronson, R. A., "Evidence that an ARG-GLY-ASP Adhesion Sequence Plays a Role in Mammalian Fertilzation", pp. 1019–1025 (1990).
Bronson, R. A., "Sperm-oolemmal Interaction: Role of the ARG-GLY-ASP (RGD) Adhesion Peptide", pp. 527–529 (Sep., 1990).
Bronson, R. A., "Capacitated Human Spermatozoa Display Fibronection (Fn) on Their Surface and Anti--Fn Antibodies Inhibit Penetration of the Zona-3 Hamster Eggs by Human Sperm", (Apr. 24–27, 1991).
Yasuzumi et al. Chem. Abst. vol. 100 (1984) p. 20987p.
Vuento et al. Chem. Abst. vol. 101 (1984) p. 107,916j.
Ruoslahti, E., et al., *Cell,* vol. 44, pp. 517–518, Feb. 28, 1986.

*Primary Examiner*—Toni R. Scheiner
*Attorney, Agent, or Firm*—Hoffmann & Baron

[57] ABSTRACT

A method for detecting the presence of infertility in mammalian male test subjects based upon failure of sperm to undergo successful capacitation. Sperm samples are given the opportunity to undergo capacitation and subsequently contacted with antibodies to polypeptides having an amino acid sequence tripeptide of Arginine-Glycine-Aspartate in their cell binding domains. Binding levels indicate the degree of capacitation and consequently the presence of infertility.

12 Claims, 5 Drawing Sheets

FIG-1 ANTI-FIBRONECTIN, ANTI-VITRONECTIN AND ANTI-LAMININ ANTIBODIES BINDING TO FRESH, CAPACITATED AND PROGESTERONE EXPOSED HUMAN SPERMATOZOA, AS DETECTED BY INDIRECT IMMUNOFLUORESCENCE.

| ANTIBODY | PERCENT SPERMATOZOA FLUORESCENT | | |
|---|---|---|---|
| | FRESH SPERM (4.1% ± 3.6 AR)[1] | CAPACITATED SPERM (8.2% ± 3.4 AR) | PROGESTERONE EXPOSED CAPACITATED SPERMATOZOA (27.1% ± 5.6 AR) |
| ANTI-Fn mAb FN-15 | 8.1 ± 3.4 | 65.4 ± 13.6* | 72.6 ± 15.4* |
| ANTI-Fn pAb F-1509 | 14.3 ± 7.8 | 84.2 ± 21.3* | 86.1 ± 13.2* |
| ANTI-Vn mAb A007 | 2.4 ± 0.3 | 34.9 ± 15.5* | 43.2 ± 17.8* |
| ANTI-Vn pAb A104 | 17.8 ± 6.3 | 61.4 ± 25.4* | 70.6 ± 19.3* |
| ANTI-Lm pAb L9393 | 11.6 ± 6.4 | 24.7 ± 9.4** | 27.1 ± 12.2** |
| RABBIT Ig CONTROL | 4.2 ± 2.1 | 5.4 ± 1.6 | 4.8 ± 3.2 |
| MOPC21 MOUSE MYELOMA PROTEIN | 0 | 0 | 0 |

[1]AR = ACROSOME REACTED SPERM
* = $p < 0.001$ COMPARED WITH CONTROL AND FRESH SPERM
** = $p < 0.05$ COMPARED WITH CONTROL AND FRESH SPERM

FRESH EJACULATED, CAPACITATED SPERM AND CAPACITATED SPERMATOZOA EXPOSED TO PROGESTERONE IN ORDER TO ACHIEVE AN ACROSOME REACTION, OBTAINED FROM FIVE FERTILE DONORS, WERE EXPOSED TO ANTI-FIBRONECTIN (Fn), ANTI-VITRONECTIN (Vn) AND ANTI-LAMININ (Lm) ANTIBODIES, OR TO CONTROL RABBIT AND MOUSE IMMUNOGLOBULINS. THE PERCENTAGE OF FLUORESCENT SPERM IS EXPRESSED AS THE MEAN ± STANDARD DEVIATION OF THE RESULTS.

FIG-2 REPETITIVITY OF ANTI-FIBRONECTIN, ANTI-VITRONECTIN AND ANTI-LAMININ ANTIBODY BINDING TO CAPACITATED SPERMATOZOA.

| PERCENT ANTIBODY-LABELLED SPERMATOZOA, MEAN ± SEM | | | | |
|---|---|---|---|---|
| | NUMBER OF TESTS | F-1509 ANTI-Fn Ab | A104 ANTI-Vn Ab | L-9393 ANTI-Lm Ab |
| DONOR 1 | 5 | 91.4 ± 4.16 | 81.6 ± 6.12 | 25.0 ± 4.11 |
| DONOR 2 | 4 | 59.7 ± 5.02 | 32.5 ± 4.29 | 22.2 ± 4.78 |
| DONOR 3 | 4 | 57.3 ± 8.45 | 61.3 ± 3.01 | 25.7 ± 3.94 |
| DONOR 4 | 3 | 91.3 ± 5.54 | 92.3 ± 6.69 | 31.3 ± 4.33 |
| DONOR 5 | 3 | 82.1 ± 8.54 | 53.3 ± 5.22 | 28.6 ± 5.04 |

SPERMATOZOA FROM DIFFERENT EJACULATES OF FIVE FERTILE DONORS, SELECTED BY SWIM-UP, WERE INCUBATED OVERNIGHT IN BWW/HSA 30 mg:ml IN ORDER TO ACHIEVE CAPACITATION. THEREAFTER, THEY WERE EXPOSED TO ANTI-Fn, Vn AND Lm ANTIBODIES AND TO FLUORESCEINATED SECOND ANTIBODY. THE MEAN AND STANDARD ERROR WAS CALCULATED FOR EACH DONOR.

FIG-3 REACTIVITY OF ANTI-FIBRONECTIN, ANTI-VITRONECTIN AND ANTI-LAMININ ANTIBODIES WITH CAPACITATED SPERMATOZOA FROM A SERIES OF FERTILE DONORS AND INFERTILE PATIENTS.

|  | DONOR NUMBER | F-1509 ANTI-Fn | A104 ANTI-Vn | L-9393 ANTI-Lm | PERCENT AR SPERM FOLLOWING PROGESTERONE |
|---|---|---|---|---|---|
| FERTILE | 1 | 89% | 85% | 17% | 27% |
|  | 2 | 83% | 91% | 42% | 32% |
|  | 3 | 94% | 78% | 2% | 29% |
|  | 4 | 100% | 94% | 33% | 41% |
|  | 5 | 72% | 51% | 29% | 37% |
|  | 6 | 81% | 63% | 19% | 28% |
| INFERTILE | 1 | 5% | 18% | 7% | 9% |
|  | 2 | 89% | 72% | 31% | 24% |
|  | 3 | 91% | 79% | 6% | 28% |
|  | 4 | 76% | 95% | 9% | 21% |
|  | 5 | 19% | 32% | 14% | 20% |
|  | 6 | 11% | 13% | 12% | 12% |
|  | 7 | 34% | 32% | – | 19% |
|  | 8 | 100% | 95% | 34% | 37% |
|  | 9 | 76% | 66% | 23% | 35% |
|  | 10 | 65% | 71% | 29% | 24% |
|  | 11 | 76% | 69% | 28% | 26% |
|  | 12 | 35% | 50% | 21% | 21% |
|  | 13 | 72% | 80% | 19% | 29% |
|  | 14 | 97% | 88% | – | 31% |
|  | 15 | 12% | 7% | 5% | 13% |
|  | 16 | 77% | 54% | 28% | 20% |
|  | 17 | 68% | 68% | 21% | 24% |
|  | 18 | 7% | 18% | 6% | 16% |
|  | 19 | 35% | 47% | 16% | 20% |
|  | 20 | 100% | 98% | 34% | 37% |

A SERIES OF SIX FERTILE DONORS AND TWENTY INFERTILE PATIENTS WERE CHOSEN FOR TESTING CAPACITATED SPERM WITH ANTI-FIBRONECTIN, ANTI-VITRONECTIN AND ANTI-LAMININ ANTIBODIES. THESE SPERMATOZOA, INCUBATED OVERNIGHT IN BWW/HSA 30 mg/ml, WERE DEMONSTRATED TO BE CAPACITATED BASED ON THEIR ABILITY OF UNDERGOING ACROSOME REACTION FOLLOWING PROGESTERONE 5 μg/ml.

FIG-4 INHIBITION OF ANTI-VITRONECTIN ANTIBODY BINDING TO CAPACITATED HUMAN SPERMATOZOA BY THEIR PRE-INCUBATION WITH FREE FIBRONECTIN OR VITRONECTIN IN SOLUTION.

| PERCENT ANTIBODY-LABELLED SPERMATOZOA, AS DETECTED BY INDIRECT IMMUNOFLUORESCENCE ||| PROTEIN-FREE CONTROL | FIBRONECTIN 1 mg/ml | VITRONECTIN 1 mg/ml |
|---|---|---|---|---|---|
| DONOR 1 || A007 | 56% | 61% | 2% |
|  || A104 | 95% | 87% | 9% |
| DONOR 2 || A007 | 73% | 59% | 0 |
|  || A104 | 100% | 88% | 4% |

A SIGNIFICANT IMPAIRMENT OF ANTI-VITRONECTIN ANTIBODY BINDING TO CAPACITATED SPERMATOZOA WAS OBTAINED BY THEIR PREINCUBATION WITH 1 mg/ml PURIFIED HUMAN VITRONECTIN, BUT NOT PURIFIED FIBRONECTIN, INDICATING THAT NO CROSS REACTION OF THESE ANTIBODIES WITH FIBRONECTIN EXISTS.

METHOD OF SCREENING FOR INFERTILITY

This application is a continuation-in-part of copending U.S. patent application Ser. No. 07/740,042 filed on Aug. 1, 1991, now U.S. Pat. No. 5,256,539.

FIELD OF INVENTION

The present invention relates to methods of screening for infertility in mammalian male test subjects. More specifically, the present invention relates to methods for detecting a lack of capacitation in a sample of spermatozoa from a test male mammal. In particular, the present invention relates to diagnostic assays using antibodies to polypeptides having a specified amino acid triplet in order to detect a lack of capacitation in a sample of mammalian spermatozoa.

BACKGROUND OF THE INVENTION

It is often useful to be able to predict the fertility of a mammalian male animal in a variety of contexts. For example, animal breeders typically go to great lengths to find male animals likely to produce offspring having desirable genetic traits. However, animal breeding is often an expensive endeavor. Males having low fertility are of reduced value due to the increased cost of breeding the animal where repeated inseminations are required to ensure impregnation. Currently, there are few reliable methods for detecting a lack of fertilizing capacity in these male animals short of statistical data compiled on their past breeding results.

Additionally, the medical community is often concerned with human fertility but has few reliable methods for evaluating the fertility of male patients. In particular, physicians have few reliable methods for detecting a lack of capacitation in the sperm of a patient.

Mammalian spermatozoa in semen cannot fertilize eggs but must undergo alterations in the plasma membrane in order to acquire fertilizing capability. The process during which the spermatozoa undergo these alterations in their membrane is termed capacitation and occurs naturally in the female reproductive tract once the sperm has been deposited.

Capacitation refers to the ability of sperm to adhere to, penetrate and fertilize susceptible ova. Penetration and fertilization not only require potentiality of the sperm to achieve a functional status, but also require that favorable conditions exist in the uterine environment. If favorable conditions exist in the mammalian uterus, sperm become capacitated and penetrate the ova. Thereafter, embryonic development begins.

To date, there have been few reliable methods for determining the fertilizing capability of the sperm of a test subject. Although it has been postulated that a variety of factors probably play a role in promoting this fertilizing capability, it is generally accepted that successful capacitation of the sperm is one of those factors. Consequently, a determination of capacitation would be a useful approach to predicting a lack of fertility in a semen specimen. Unfortunately, there are no reliable methods currently available for detecting a lack of capacitation in mammalian sperm.

It is therefore an object of the present invention to provide a method for detecting the presence of infertility in a mammalian male test subject based upon a lack of capacitation.

It is a further object of the present invention to provide a method for detecting a lack of capacitation in a sample of sperm from a mammalian male test subject.

SUMMARY OF THE INVENTION

The present invention is a method for detecting the presence of infertility in mammalian males, especially humans, due to a lack of capacitation. The method involves exposing a sample of sperm from the donor subject to in vitro conditions that are favorable for inducing capacitation for a period of time sufficient for capacitation to occur. In other words, the sperm sample must be provided with sufficient opportunity to undergo its potential for capacitation.

After the sperm sample has been given sufficient opportunity to undergo capacitation, the sample is contacted with one or more monoclonal or polyclonal antibodies directed against a polypeptide characterized by an amino acid sequence which comprises an Arginine-Glycine-Aspartate triplet contained within its cell binding domain for a sufficient period of time and under conditions suitable for permitting the antibody to bind to the sperm surface. Subsequently, an evaluation and determination of the degree of antibody binding may be performed in order to detect a lack of capacitation, and, consequently, a lack of fertilizing capability.

As previously mentioned, there are few reliable methods currently available for detecting a lack of fertilizing capability in mammalian sperm. Moreover, there are no reliable methods for determining a lack of capacitation in a mammalian semen specimen.

The present invention advantageously provides a novel method for determining whether or not a sample of mammalian sperm has undergone successful capacitation. Although it has recently been discovered that certain polypeptides containing the tripeptide Arginine-Glycine-Aspartate in their cell binding domains will competitively inhibit sperm-oolemmal adhesion and penetration of hamster ova that have been contacted with capacitated sperm, there is no conclusive data available to date regarding the precise role of such polypeptides in sperm capacitation. Additional evidence related to sperm-oolemmal interaction suggests that receptors for peptides containing the Arginine-Glycine-Aspartate tripeptide, hereinafter referred to as RGD, are present on the surface of mammalian ova. Consequently, it has been postulated that RGD-containing peptides may somehow be involved in mammalian sperm-oolemmal interaction. For example, recent data has been provided indicating that fibronectin, a RGD-containing peptide, is present on the surface of capacitated sperm as well as acrosome reacted sperm. Unfortunately, further evidence regarding capacitation and the mechanisms by which it occurs have been unavailable to date.

It has now been discovered that a significant increase in the expression of various RGD-containing polypeptides occurs on the surface of capacitated sperm as compared with non-capacitated sperm. Examples of such polypeptides include the surface ligand glycoproteins vitronectin, fibronectin and laminin. Accordingly, the method of the present invention employs this discovery by providing a new approach for determining a lack of capacitation in a mammalian sperm sample as described below. Consequently, the present invention will afford physicians as well as veterinarians a useful tool in diagnosing fertility problems.

DETAILED DESCRIPTION

In accordance with the preferred embodiment of the method of the present invention, a semen sample is obtained from the test subject. Subsequently, an acceptable separation and isolation procedure is performed to separate the sperm component from the seminal vehicle. Although the following embodiments are illustrated in terms of a human sperm sample, the method of the present invention is equally applicable to sperm samples of other mammalian species with the exception of minor modifications where indicated.

For example, an acceptable approach for separation and isolation includes injecting 300 microliters of semen under 2 milliliters of Biggers-Whitten-Whittingham (BWW) medium containing 5 mg/ml of serum albumin, preferably obtained from the same genus and species as the test subject. A 100 milliliter preparation of BWW should generally include 490.2 mg NaCl, 35.6 mg KCl, 16.2 mg $KH_2PO_4$, 29.4 mg $MgSO_4$, 2.8 mg sodium pyruvate, 100 mg dextrose, 300 mg $NaHCO_3$, 52.7 mg calcium lactate, 0.368 sodium lactate, 7.5 mg penicillin G, 7.5 mg streptomycin sulfate and 0.02% phenol red.

The medium containing the semen sample is subsequently incubated for 60 minutes at 37° C. under an air mixture having a 5% $CO_2$ component. Following incubation, the mixture containing motile sperm is collected and centrifuged at 600 g's and the sperm component is resuspended to a concentration of $20 \times 10^6$ cells/ml using BWW medium having a serum albumin concentration of 30 mg/ml. If sperm samples from other mammalian species are to be isolated, the appropriate modifications to the medium for capacitating sperm should be incorporated accordingly.

Upon completion of the separation and isolation step, the sperm sample is exposed to in vitro conditions sufficient for inducing capacitation. Inducing successful capacitation in vitro requires the presence of a sufficient amount of serum albumin in contact with the sperm sample. These amounts may differ according to the concentration of the sperm and the species from which the sample is obtained, however, this amount is readily calculated from existing data available to those in the art. For example, at concentrations ranging from $5 \times 10^6$ cells/ml to $20 \times 10^6$ cells/ml, human sperm generally requires exposure to human serum albumin in concentrations ranging from about 5 mg/ml to about 30 mg/gl.

An example of one acceptable protocol for inducing capacitation involves incubating the sperm sample overnight at 37° C. under air having a 5% $CO_2$ component. Alternatively, the period of incubation can be shortened by increasing the osmolality of the medium from 385 to 410 mOsm.

Upon completion of the incubation step employed to induce capacitation, the treated sperm sample is subsequently contacted with appropriate monoclonal or polyclonal antibodies directed against a polypeptide which is characterized by an amino acid sequence that includes an Arginine-Glycine-Aspartate (RGD) triplet in its cell binding domain. The contact between the antibody and the sample should occur for a sufficient period of time and under conditions suitable for permitting binding of the antibody with the sperm.

Preferably, the polypeptide is selected from a group or family of peptides known as surface ligand glycoproteins which commonly occur on the surface of biological molecules. In a more preferred embodiment of the method of the present invention, the glycoprotein selected should originate from the same genus and species as the test subject from which the sperm sample was obtained. Examples of the most preferable surface glycoproteins include vitronectin, fibronectin and laminin. Alternatively, fragments of glycoproteins can be employed, provided that the cell binding region containing the RGD tripeptide remains intact within the resulting fragment and that the fragments are sufficiently immunoreactive for evoking an adequate antibody response.

For example, if the method of the present invention were employed to screen a sample of human sperm, the sperm would be most preferably contacted with monoclonal or polyclonal antibodies directed against human vitronectin, fibronectin or laminin. Alternatively, the sperm could be contacted to antibodies directed against peptide fragments of human vitronectin, fibronectin or laminin, provided that the cell binding domain of the protein remains intact within the peptide fragment, as previously discussed.

Additionally, the polypeptide employed in the method of the present invention can be a synthetic peptide having an amino acid sequence substantially corresponding to the amino acid sequence of one of the glycoproteins mentioned above. It is known in the art of protein chemistry that an identical copy of a particular polypeptide can be readily produced where every amino acid in the copy appears in exactly the same sequential position as it does in the original. In short, the copy has an amino acid sequence which corresponds exactly to the amino acid sequence of the original polypeptide from which it was copied. Alternatively, certain amino acids in the copy can be substituted with natural or synthetic amino acid analogs without altering any of the desired biological characteristics of the resulting polypeptide, provided that the regions containing biologically important residues are conserved.

For example, certain synthetic amino acid analogs can be substituted at desired positions within an amino acid sequence to impart resistance to proteolytic cleavage while maintaining the desired immunological character of the resulting polypeptide. Therefore, an identical copy of a particular polypeptide can receive certain substitutions at non-conserved regions and still retain the same biological character as the original polypeptide from which it was copied.

Consequently, the polypeptide employed in the method of the present invention can be a synthetic copy of one of the glycoproteins mentioned above, wherein the amino acid sequence of the copy corresponds substantially to the amino acid sequence of the glycoprotein from which it was copied. The synthetic copy can receive certain substitutions with natural or synthetic amino acid analogs, provided that the synthetic copy is capable of evoking a suitable antibody response and that the amino acid sequence of the copy conserves the cell binding domain of the original glycoprotein. Alternatively, fragments of these synthetic peptides may also be employed, taking into account the same considerations previously mentioned for fragments of the original glycoprotein.

A variety of techniques for synthesizing polypeptides are available in the art. For example, a variety of automated synthesis units are currently available including the NPS 4000 semi-automated multichannel peptide synthesizer and the Biosearch Model 9600 automatic peptide synthesizer. Alternatively, certain recombinant DNA techniques or proteolytic cleavage techniques may be incorporated for constructing the polypeptide of the present invention. For example, a carefully orchestrated proteolysis of a naturally occurring glycoprotein would be an acceptable method for producing a synthetic polypeptide for the present invention. Accordingly, the term "synthetic polypeptide", as it appears throughout the present Application, is taken to mean any non-naturally-occurring polypeptide constructed by one of the methods mentioned above or by other suitable methods known in the art.

Despite the nature of the polypeptide selected, the method of the present invention relies primarily upon the effectiveness of the monoclonal or polyclonal antibody utilized to screen the semen sample in order to determine the extent of capacitation. While it would be acceptable to independently develop monoclonal or polyclonal antibodies to RGD-containing polypeptides using established and readily available immunological protocols, the preferred embodiment of the present invention utilizes several commercially available antibodies and one non-commercial antibody when the method of the present invention is being used for screening human sperm.

One of the preferred, commercially available antibodies mentioned above is F-1509, a goat-derived polyclonal antibody directed against human plasma fibronectin obtained from Sigma Chemical Co. in a stock concentration of 6.5 mg/ml. Another preferred antibody is a murine IgG1 monoclonal antibody directed against human plasma fibronectin, FN-15, also obtained from Sigma Chemical Co. in a stock concentration of 5 mg/ml. A third preferred antibody is a non-commercial murine monoclonal antibody directed against human cellular fibronectin and is denoted as A134. It can be obtained from ADEZA Biomedical in Sunnyvale, Calif. Two additional preferred, commercially available antibodies include a rabbit-derived polyclonal antibody directed against human vitronectin (Code No. A104) and a murine monoclonal also directed against vitronectin (Code No. A007), both obtained from Telios Pharmaceuticals in San Diego, Calif. Rabbit-derived polyclonal antibody directed against human laminin was purchased from Sigma Chemical.

In cases where the present invention is utilized to screen other species of mammalian sperm in order to detect a lack of capacitation, it is preferential to either obtain or manufacture antibodies directed against glycoproteins or other RGD-containing polypeptides that have been specifically isolated from the species to be screened, especially if a reliable level of specificity is to be maintained. Commercial antibodies directed against other such polypeptides are also available for evaluating the sperm of other mammalian species. For example, if an investigator desired to screen bull semen in order to detect a low level of capacitation, it would be preferential to use antibodies that had been directed specifically against bovine glycoproteins.

In the preferred embodiment of the present invention, the immunoreaction is conducted over a three hour period at 37° C. under air having a 5% $CO_2$ component. Additionally, the ratio of sperm to antibody should be calculated based upon the titre of the antibody used. For human sperm, for example, at a concentration ranging from about $1 \times 10^6$ motile sperm/ml to about $4 \times 10^6$ motile sperm/ml, the antibody concentration should be about 20 mg/mL to about 200 mg/ml.

EXAMPLE 1

Each of 3 separate aliquots containing 190 microliters of human spermatozoa (concentration=$20 \times 10^6$ cells/ml), which had previously been exposed to sufficient in vitro conditions for inducing capacitation, were initially exposed for three hours at 37° C. under air having a 5% $CO_2$ component to 10 microliters of each of the aforementioned antibodies, FN-15, F-1509 and A134, respectively. Monoclonal antibody FN-15 and polyclonal antibody F-1509 were tested at several dilutions, ranging from 1:20 to 1:2000.

Alternatively, each sample can be immunoreacted with a combination of polyclonal and monoclonal antibodies directed against fibronectin as long as the subsequent steps involved in determining the binding status of the antibodies to the sample incorporate an appropriate combination of secondary antibodies to ensure accurate detection of binding.

For example, if murine and bovine antibodies to human plasma fibronectin are co-incubated with a human sperm sample to increase the sensitivity of the assay, appropriate anti-bovine and anti-murine secondary antibodies must be incorporated so that detectable immunocomplexes can be formed. However, it should be noted that the greater the number of different fibronectin antibodies contacting the sperm sample, the greater the chance for non-specific cross reactivity. Consequently, when several different antibodies are used per sample, proper controls should be implemented to alert the investigator to any problems with cross reactivity.

Once the co-incubation of the sperm sample and the antibody has been completed, the resulting sperm-antibody complex is washed of any free antibody and resuspended in phosphate buffered saline (PBS) containing serum albumin, prior to the addition of secondary antibodies used in the detection and determination of antibody binding.

EXAMPLE 2

One hundred microliters of each of the sperm/antibody suspensions produced in Example 1 was placed in a Beckman E Microcentrifuge where the antibody-labelled sperm were pelleted at 12,000 rpm for 8 seconds and the medium containing the free antibodies was collected and removed. Each pellet was resuspended in 100 microliters of PBS containing 5 mg/ml of bovine serum albumin (BSA). The wash procedure was repeated twice thereafter.

After the sperm has been washed free of any unbound antibodies to fibronectin, detection and determination of bound antibody is performed in order to assess whether there is a lack of capacitation as indicated by a low level of anti-fibronectin antibody binding.

In the preferred embodiment of the method of the present invention, immunofluorescence and immunobead binding techniques are used. In particular, these techniques allow an investigator to score individual spermatozoa in order to determine the proportion of sperm expressing fibronectin or other RGD-containing polypeptides on their surface. Although other immunological detection methods may work as effectively, it is important to note that the method selected must provide for accurate scoring of the sperm if reliable quantitative binding results are to be obtained.

EXAMPLE 3

For immunofluorescence, each of the pre-washed, 100 microliter resuspensions of Example 2, which contained the antibody-labelled sperm, were treated with the appropriate secondary antibody in order to detect the presence of bound monoclonal or polyclonal antibodies to fibronectin. The F-1509 labelled sperm was treated with FITC-conjugated rabbit anti-goat IgG antibody per enclosed instructions as obtained from Jackson Immunoresearch in West Grove, Pa. The A134 labelled sperm and the FN-15 labelled sperm were treated with a FITC-conjugated F(ab')$_2$ fragment of sheep anti-mouse IgG per enclosed instructions as obtained from Sigma Chemical Co. Each of the secondary antibodies was diluted to 1/20th of their original stock concentrations upon addition to the respective one hundred microliter samples. The antibody-labelled sperm were then incubated in the presence of the second antibody for one hour in the absence of light. Each sample was subsequently washed to remove any unbound secondary antibody using the wash protocol as described in Example 2 above. Each sample was resuspended to a concentration of $2$–$5 \times 10^6$ sperm/cc in PBS having 5 mg/ml of BSA and evaluated for fluorescence using a 520 nm filter under UV illumination.

EXAMPLE 4

For immunobead binding, 0.5 mg of immunobeads coated with rabbit anti-mouse immunoglobulin, heavy and light chain specific, obtained from BioRad, Richmond, Calif., was washed in PBS containing 5 mg/ml of BSA and centrifuged at 6,000 rpm for 3 minutes. The wash step was repeated 4 times and the beads were resuspended in 1 milliliter of PBS with 5 mg/ml of BSA in preparation for contact with the monoclonal antibody-labelled sperm, the FN-15 labelled sperm and the A134 labelled sperm. Similarly, 8 mg of immunobeads coated with rabbit anti-goat immunoglobulin, obtained from BioRad, was washed according to the wash protocol used for the rabbit anti-mouse immunobeads and subsequently resuspended in 1 milliliter of PBS with a BSA concentration of 10 mg/ml in preparation for contact with the polyclonal antibody-labelled sperm, F-1509 labelled sperm. Duplicate suspensions of the antibody-labelled sperm were prepared using the methods and materials set forth in Examples 1 and 2 above. Subsequently, a 100 microliter suspension of each of the 3 antibody/sperm complexes was pelleted by centrifugation and resuspended in BWW media with 5 mg/ml of HSA to a concentration of $5$–$10 \times 10^6$ cells/ml. Fifty microliters of beads and 5–10 microliters of sperm were mixed in a serologic tube, placed on a slide and observed within 10 minutes under phase contrast optics (640×), in order to score sperm carrying beads. At least 100 motile sperm were scored. Only those sperm swimming within the bead suspension, observed to collide with immunobeads, were scored for bead binding.

Examples 3 and 4 are merely illustrative of two acceptable techniques known in the art which can be utilized in conjunction with the method of the present invention for detecting and determining the degree of antibody binding as an indicator of capacitation. With respect to the techniques as applied in Examples 3 and 4, statistical analysis was performed as set forth below in Example 5 below.

EXAMPLE 5

The percent of spermatozoa displaying fibronectin on their surfaces in different experiments was expressed as a mean±standard deviation (SD). Comparison of the results obtained with immunofluorescence and immunobead binding in the evaluation of anti-fibronectin antibody binding to spermatozoa was made using Student's "t" test for paired samples. No significant difference in the percent of sperm displaying fibronectin was found using immunofluorescence or immunobead binding. For F-1509, the mean±SD of sperm displaying fibronectin was 80.9±18.4% and 68.8±33.7% respectively for fertile donors and infertile patients as detected with IF (range 37–100% and 5–100%, median 83 and 79), and 75.1±21.8% and 57.2±32.6% with immunobead binding (range 24–95% and 6–100%, median 80 and 60). For FN-15, the mean±SD of sperm displaying fibronectin as detected with IF was 63.1±23.4% and 62.3±25.7% respectively for fertile donors and infertile patients (range 19–86% and 19–97%, median 68 and 65), and 55.7±15.9% and 43.8±21.7% with immunobead binding (range 28–74% and 11–81%, median 59.5 and 45). For A134, the mean±SD of sperm displaying fibronectin was 58.7±27.2% and 70.8±28.8% for fertile donors and infertile patients, respectively, (range 28–80% and 27–100%, median 68 and 82.5) as detected with IF, and 55.3±22.8% and 66.4±27.1%, respectively, using immunobead binding (range 29–69% and 31–100%, median 68 and 69.5). Regional expression of fibronectin appeared to be predominantly on the sperm head, as detected by immunobeads. In contrast, differences in the region of fibronectin between spermatozoa from the same ejaculate were observed using immunofluorescence. The entire sperm surface was positive for the majority of spermatozoa (approximately 85%), while others showed an irregular fluorescence on their surfaces. Even when the entire sperm surface was fluorescent, some areas were brighter than others, varying for each spermatozoa without any particular regional association.

EXAMPLE 6

Additional experiments were performed to determine the degree of successive capacitation on several samples of human sperm utilizing antibodies to various human surface ligand glycoproteins, namely vitronectin, fibronectin and laminin. Spermatozoa were obtained by swim-up from 6 health doners whose specimens were normal according to the World Health Organization criteria. Additional samples were obtained from 20 patients referred for semen analysis to the Center for Infertility of the Department of Obstetrics and Gynecology of the University of Milano, San Raffaele Hospital. All the patients whose sperm were utilized presented samples with at least $10 \times 10^6$ spermatozoa/ml and 20% progressive motility. In all cases, motile sperm were selected by swim-up. Three hundred microliters of semen was injected under 2 ml Bigger-Whitten-Whittingham (BWW) medium containing 5 mg/ml of human serum albumin (HSA obtained from Sigma Chem. Co., St. Louis, Mo.) into 15 ml conical tubes. After a 60 minute incubation at 37° under a 5% $CO_2$/air mixture, medium containing motile sperm was collected from all the tubes prepared with the same sperm sample, pooled and centrifuged at $600 \times g$. The spermatozoa were resuspended to a concentration of $20 \times 10^6$ cells/ml in BWW/HSA 30 mg/ml. Thereafter, sperm were divided into 250 μl aliquots, and either capacitated by incubation overnight at 37° under a 5% $CO_2$/air mixture, or utilized as fresh sperm in order to study fibronectin, vitronectin and laminin expression as well as the degree of spontaneous acrosome reaction.

EXAMPLE 7

Acrosome reactions were induced in capacitated spermatozoa utilizing progesterone according to methods known in the art. One milligram of progesterone was dissolved in 0.1 ml of absolute ethanol and diluted with 0.9 ml of phosphate buffered saline (PBS). This stock solution was diluted with BWW having a HSA concentration of 30 mg/ml in order to reach a 100 μg/ml progesterone concentration. Five microliters of diluted stock solution was added to 95 μl of capacitated spermatozoa ($20 \times 10^6$) in order to obtain a final concentration of 5 μg/ml per 0.5 ml Eppendorf microcentrifuge tubes. After 1 hour incubation at 37° under a 5% $CO_2$/air mixture, the sperm were washed by three centrifugations at 12000 rpm for 8 seconds with approximately 0.5 ml of BWW/HSA 5 mg/ml. Thereafter, the sperm were resuspended in 100 μl BWW/HSA 30 mg/ml (concentration of $20 \times 10^6$ cells/ml) and studied for fibronectin, laminin and vitronectin expression and degree of acrosome reaction.

EXAMPLE 8

The percentage of fresh and capacitated spermatozoa that had spontaneously acrosome reacted, as well as that of capacitated sperm following their exposure to progesterone, was determined by means of Pisum sativum agglutinin (PSA)-FITC staining. Dead spermatozoa, which could have undergone degenerative loss of acrosomal contents, were identified with a supravital stain H258. Ninety microliters of $20 \times 10^6$ sperm in BWW 30 mg/ml HSA were incubated 5 minutes at 37° C. in 5% $CO_2$ with 25 μl of H258, 10 μg/ml in PBS. After incubation, the sperm were prepared for acrosomal assessment by stratification over 250 μl of 2% PVP (polyvinylpyrrolidone) in PBS. The sperm were subsequently centrifuged for 10 minutes at $900 \times g$. The pellet was resuspended in 100 μl of 95% ethanol in PBS and incubated at 4° C. for 30 minutes. Thereafter, a drop of sperm suspension was placed on each slide at room temperature. Upon evaporation of the ethanol, the slide was covered with 20 μl of 100 μg/ml PSA-FITC and incubated in the dark in a humid chamber for 5 minutes. The slides were then rinsed in distilled water and mounted. Only live sperm which had not appeared fluorescent through a 480 nm filter for excitation of H258 were scored under fluorescent illumination using a 520–540 nm filter. The sperm were divided into "acrosome intact" and "acrosome reacted" once the acrosome appeared uniformly green fluorescent and when no fluorescent staining or only an equatorial green band was evident.

EXAMPLE 9

Polyclonal goat-derived antibodies to human plasma fibronectin were obtained from Sigma Chem. Co. (Code F-1509) at a stock concentration of 6.5 mg/ml. Murine monoclonal antibody IgG1 FN-15, obtained from Sigma Chem. Co. at a stock concentration of 5 mg/ml, was produced against human plasma fibronectin, but also reacts with cellular fibronectin. Polyclonal rabbit-derived antibody to human vitronectin was obtained from Telios Pharmaceuticals, San Diego, Calif., (Code A104) and was resuspended from lyophilized product at a 1 mg/ml concentration in PBS. Murine monoclonal antibody to human vitronectin, also obtained from Telios Pharmaceuticals (Code A007), was also resuspended at the 1 mg/ml concentration in PBS. Rabbit anti-laminin polyclonal antibody, 1 mg/ml, was purchased from Sigma. A mouse myeloma protein, MOPC21, of the same IgG1 subclass as the monoclonal antibodies obtained from Sigma Chem. Co., was utilized as a negative control. The protein was resuspended at a concentration of 3 mg/ml. In addition, non-immune rabbit immunoglobulin, obtained from Dako Corporation, Copenhagen, DK at a stock concentration of 5 mg/ml, was utilized as a further control. One hundred ninety microliters of $20 \times 10^6$ cells/ml of human spermatozoa were initially exposed for 1 hour at 37° C. under 5% $CO_2$ to 10 μl each of the anti-fibronectin, anti-laminin antibodies, control mouse myeloma protein or control rabbit immunoglobulins. Anti-vitronectin antibodies were further diluted 1:10 prior to the addition of 10 μl to the 180 μl of sperm, given the high affinity of these antibodies for vitronectin. The final concentration of each of anti-fibronectin, anti-laminin and anti-vitronectin antibody was the concentration suggested by the manufacturer for indirect immunofluorescence studies.

One hundred microliters of sperm suspension, containing $2 \times 10^6$ spermatozoa and exposed to the anti-fibronectin, anti-laminin or anti-vitronectin antibodies, were placed in microcentrifuge tubes. The spermatozoa was subsequently washed three times with PBS having a BSA concentration of 5 mg/ml in a centrifuge at 3000 rpm for 8 seconds. The pellet of spermatozoa was resuspended in 100 μl of PBS containing 5 mg/ml of BSA. Fluorescenated secondary antibodies were employed at final dilution of 1:20 in a volume of 100 μl to detect primary antibodies directed against fibronectin, vitronectin or laminin which had become bound to spermatozoa. Since goat-derived antibodies to fibronectin (F-1509, obtained from Sigma Chemical Co.) were utilized to detect fibronectin present on the sperm sample, a FITC-conjugated anti-goat IgG secondary antibody was employed. In contrast, a FITC-conjugated goat anti-rabbit immunoglobulin was provided to detect anti-laminin and anti-vitronectin antibodies, as well as rabbit control immunoglobulins. Additionally, FITC-conjugated F(ab')$_2$ fragments of sheep anti-mouse IgG was employed for monoclonal antibody detection. Spermatozoa were incubated in the presence of secondary antibody at room temperature for 1 hour in the dark. Thereafter, they were washed three times as described above, and sperm fluorescence was evaluated utilizing a 520 nm filter under UV illumination.

EXAMPLE 10

In a second series of experiments, capacitated spermatozoa were exposed to A104 anti-vitronectin polyclonal antibody and A007 monoclonal antibody in the presence of varying concentrations of purified human vitronectin, obtained from Telios Pharmaceuticals, in order to assess the specificity of anti-vitronectin antibody binding to the sperm surface. Final concentrations of free vitronectin varied from 50 µg/ml to 1 mg/ml.

To test the specificity of polyclonal and monoclonal anti-vitronectin antibody for vitronectin and to exclude the possibility of a cross reaction of these antibodies with fibronectin, two experiments were performed using BWW solutions containing either monoclonal or polyclonal anti-vitronectin antibody at 10 µg/ml, fibronectin or vitronectin at 1 mg/ml, or, alternatively free medium as a control. Two hundred microliters of capacitated spermatozoa were centrifuged at 1800 rpm for 10 minutes and the pellet was resuspended in 200 µl of each of the prepared solutions. Incubation for antibody binding detection was performed as above described.

EXAMPLE 11

Motile spermatozoa from three fertile doners were obtained by swim-up and capacitated as previously described. Thereafter, spermatozoa were pooled, washed carefully by means of two centrifugations at 1800 rpm for 10 minutes and finally resuspended to $100 \times 10^6$ cells/ml in Chaps lysis buffer. The Chaps lysis solution contained 0.3% Chaps (3-[3-Cholamidopropyl-dimethylammonio]-1-propane-sulfonate), 140 mMNaCl, 2 mM PMSF, 8 mM Iodacetamide and 10 mM Tris. After 30 minutes incubation at 4° C., tubes containing spermatozoa were centrifuged for 10 minutes at 3000 rpm. Thereafter, the pellet was discarded and the supernatant was subjected to Dot-blot analysis in order to test for the presence of fibronectin and vitronectin.

EXAMPLE 12

Two experiments were performed using standard Dot-blot analysis techniques. The first experiment was performed to show the absence of fibronectin and vitronectin in the media used for sperm washing and capacitation. The second experiment was performed to demonstrate the presence of fibronectin and vitronectin in the solubilized sperm membrane. In all of the experiments, 2 µl of the solutions to be tested were spotted on individual 1.0×1.0 cm nitrocellulose paper strips. The strips were allowed to dry and were subsequently incubated for 1 hour in a blocking solution consisting of PBS containing 0.3 mg/ml of BSA. The strips were then incubated for 2 hours in a solution of PBS containing 1% BSA, 0.05% Tween 20 and the anti-fibronectin or anti-vitronectin monoclonal antibody at a dilution of 1:1500. Thereafter, the strips were washed four times with PBS containing 1% BSA and 0.05% Tween 20. The strips were subsequently incubated for 1 hour with alkaline phosphatase-conjugated rabbit anti-mouse immunoglobulin at a dilution of 1:1000 in the same buffer. After accurate washing with PBS/BSA/Tween 20, the strips were exposed to substrate solution of BCIP/NBT, obtained from Bio-Rad, for 15 minutes at room temperature. The presence of antigen was demonstrated by the development of purple spots on the nitrocellulose paper strips.

EXAMPLE 13

Figure 1:
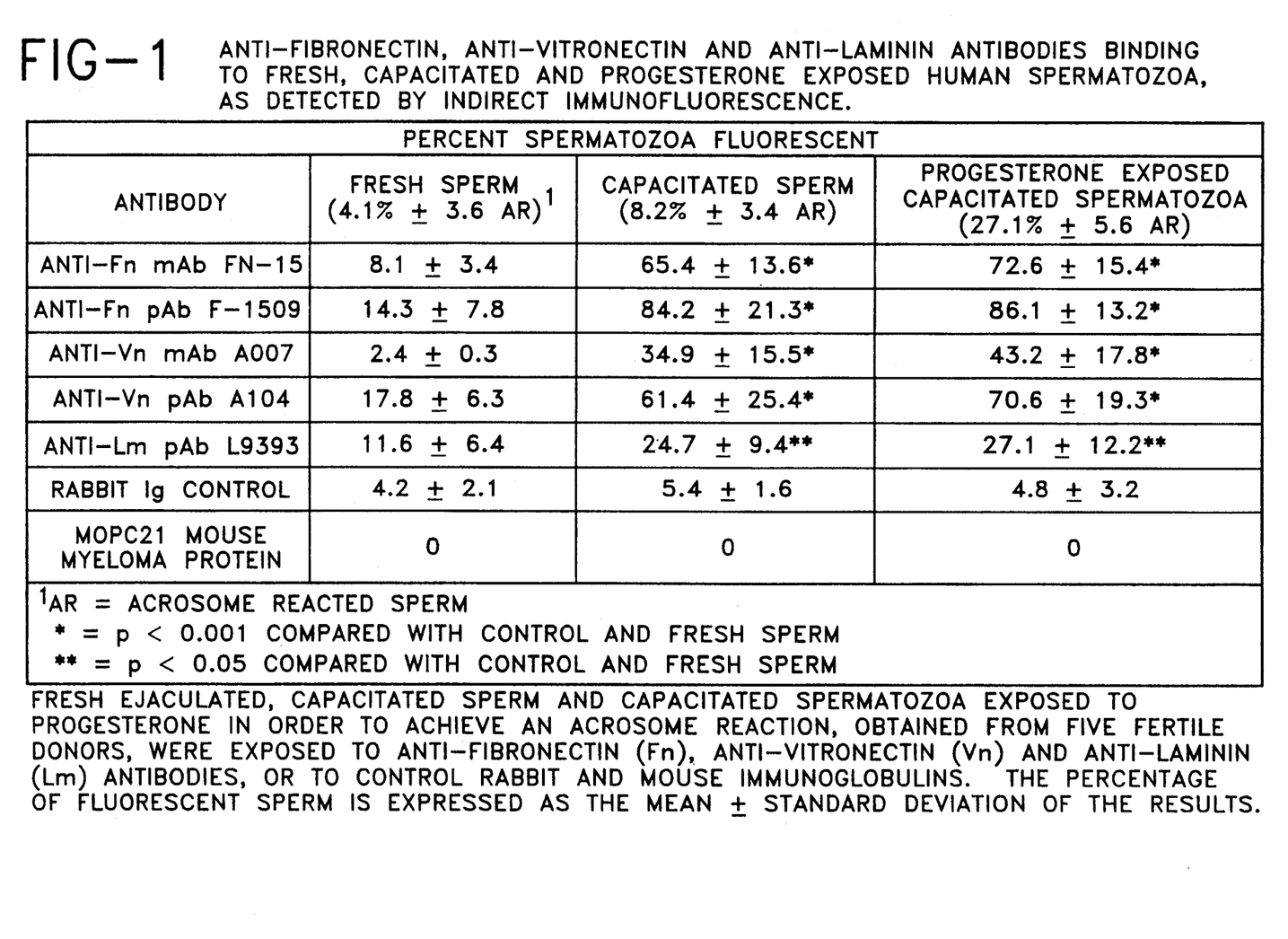
FIG. 1 illustrates anti-fibronectin, anti-vitronectin and anti-laminin antibodies binding to fresh capacitated and progesterone-exposed human spermatozoa, as detected by indirect immunofluorescence.

The presence on the sperm surface of fibronectin, laminin and vitronectin was detected by means of antibodies directed against these proteins. The percent spermatozoa reacting with anti-fibronectin and anti-vitronectin antibodies increased significantly when spermatozoa were capacitated or exposed to progesterone in order to induce an acrosome reaction. Fresh spermatozoa were substantially negative for binding (see FIG. 1). No significant differences were observed between spermatozoa incubated overnight in BWW solution to induce capacitation and capacitated spermatozoa exposed to progesterone, although the percent acrosome reacted sperm was different (8.2±3.4 versus 27.1±5.6). Polyclonal antibodies were observed to react with a higher percentage of spermatozoa than monoclonals, but a significant binding, compared to control, was also noted for monoclonal antibodies. The percent of capacitated spermatozoa reacting with polyclonal anti-laminin antibodies was lower than that observed for anti-vitronectin and anti-fibronectin, although a significant difference ($p<0.05$) was observed when compared to fresh sperm and control. With respect to the regional expression of proteins on the sperm surface, significant differences were noted between the three proteins, as judged by the different fluorescence patterns. While fibronectin was uniformly present on the sperm surface, more precise localizations were observed for vitronectin and laminin. Laminin was not detected on sperm head, but appeared to have a uniform tail localization. Anti-vitronectin antibodies bound to the equatorial region of the sperm head, resulted in a strongly fluorescent band upon exposure to fluoresceinated second antibody.

EXAMPLE 14

Figure 2:
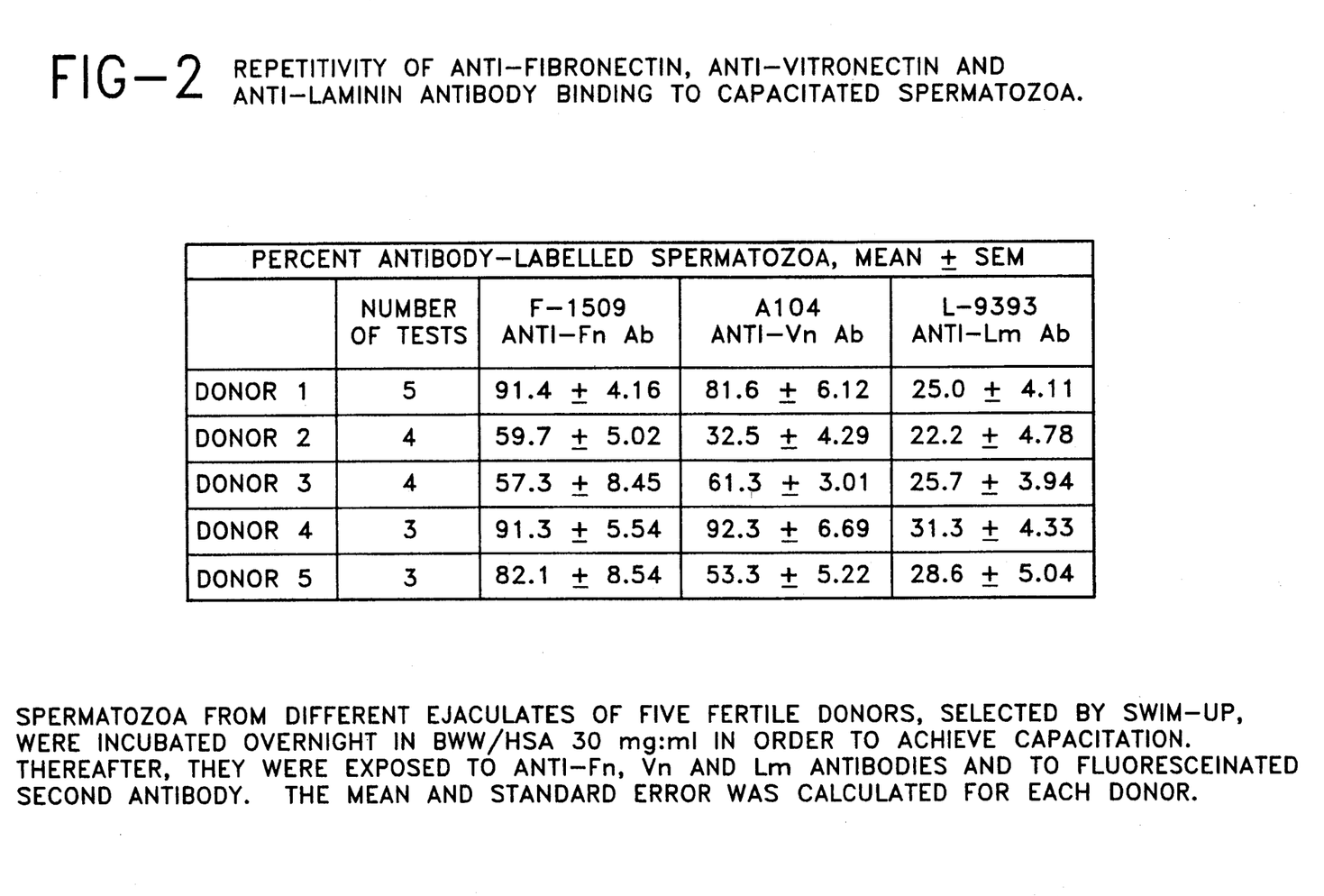
FIG. 2 illustrates repetitivity of anti-fibronectin, anti-vitronectin and anti-laminin antibody binding to capacitated spermatozoa.

As capacitated sperm bound anti-fibronectin, anti-vitronectin and anti-laminin antibodies at a stronger extent than fresh spermatozoa, studies to assess the repetitivity of results were done on spermatozoa incubated overnight in BWW/HSA 30 mg/ml. The results are set forth in FIG. 2. The percent spermatozoa reacting with the same antibodies was similar for different ejaculates of the same donor, although a wide range of reactivity was observed between different donors.

EXAMPLE 15

Sperm obtained from a series of six fertile donors and 20 infertile patients was incubated overnight in a BWW solution containing 30 mg/ml of human serum albumin and was subsequently utilized to test the different reactivity of polyclonal antibodies to vitronectin, fibronectin and laminin. The results are set forth in FIG. 3. For fertile donors, the percent spermatozoa reacting with anti-fibronectin varied from 72 to 100%; with anti-vitronectin, from 51 to 94%; and, with anti-laminin, from 2 to 42%. The aforementioned percentage ranges included means of 86.5±9.97 (mean+SD), 77.12±16.7 and 23.67±14.07, respectively and medians of 86, 81.5 and 24, respectively. For infertile patients, the range was much wider. For anti-fibronectin antibody, the percent of fluorescent spermatozoa varied from 5 to 100%; for anti-vitronectin from 7 to 98%; and, for anti-laminin, from 5 to 34%. The means (±standard deviation) of binding were 57.25±33.66, 56.55±29.13, and 19.06±10.16, respectively, and the medians were 70, 60 and 19, respectively. The percent spermatozoa able to undergo an acrosome reaction following exposure to progesterone varied widely (from 9 to 41%), but the samples which were not able to have a significant percent of acrosome reacted sperm (n 1, 6, 15), also displayed an irrelevant reactivity with the three antibodies, perhaps suggesting a defect of the mechanisms of capacitation, with no changes of antigen expression.

EXAMPLE 16

Figure 3:
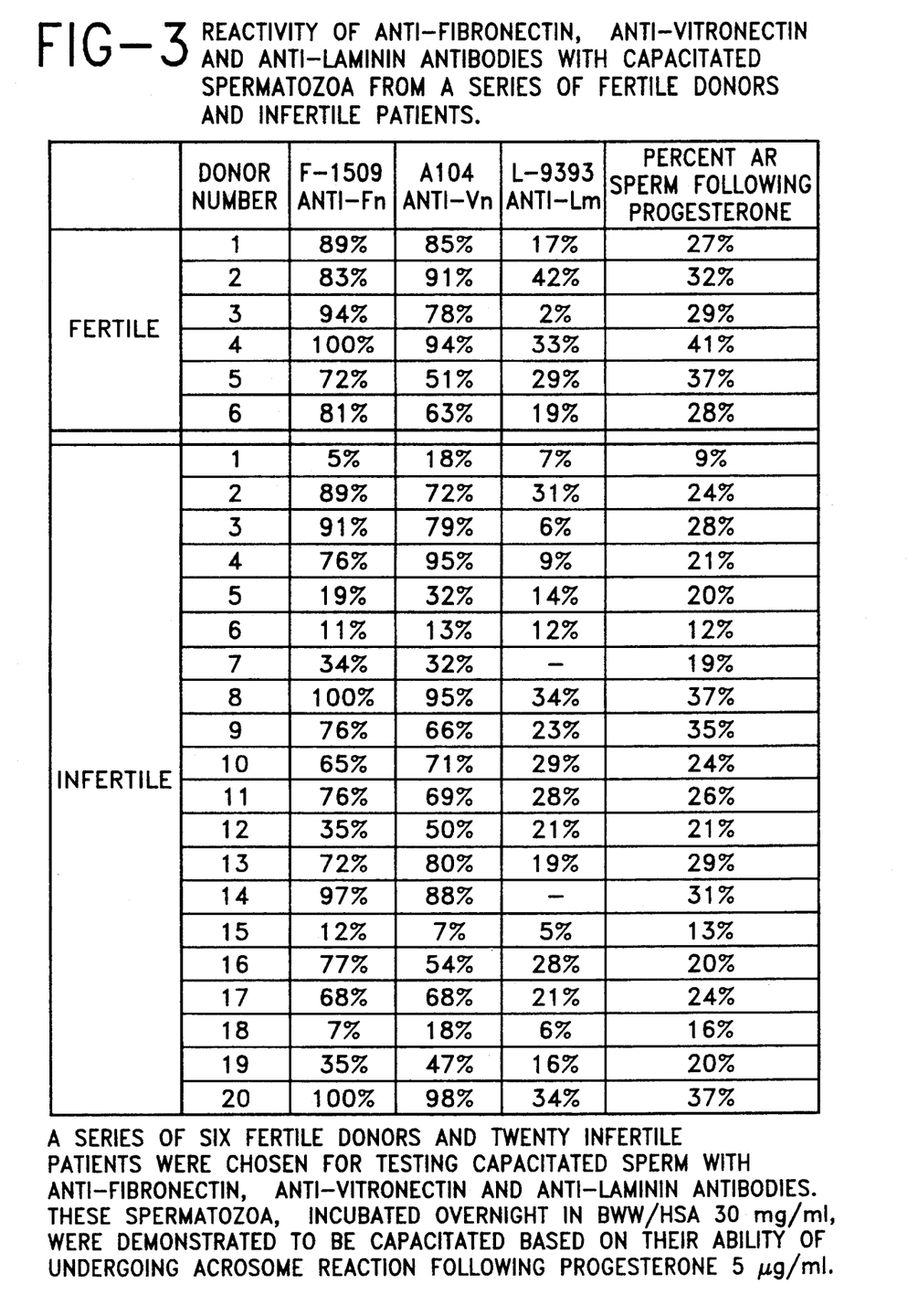
FIG. 3 illustrates reactivity of anti-fibronectin, anti-vitronectin and anti-laminin antibodies with capacitated spermatozoa from a series of fertile donors and infertile patients.
Figure 4:
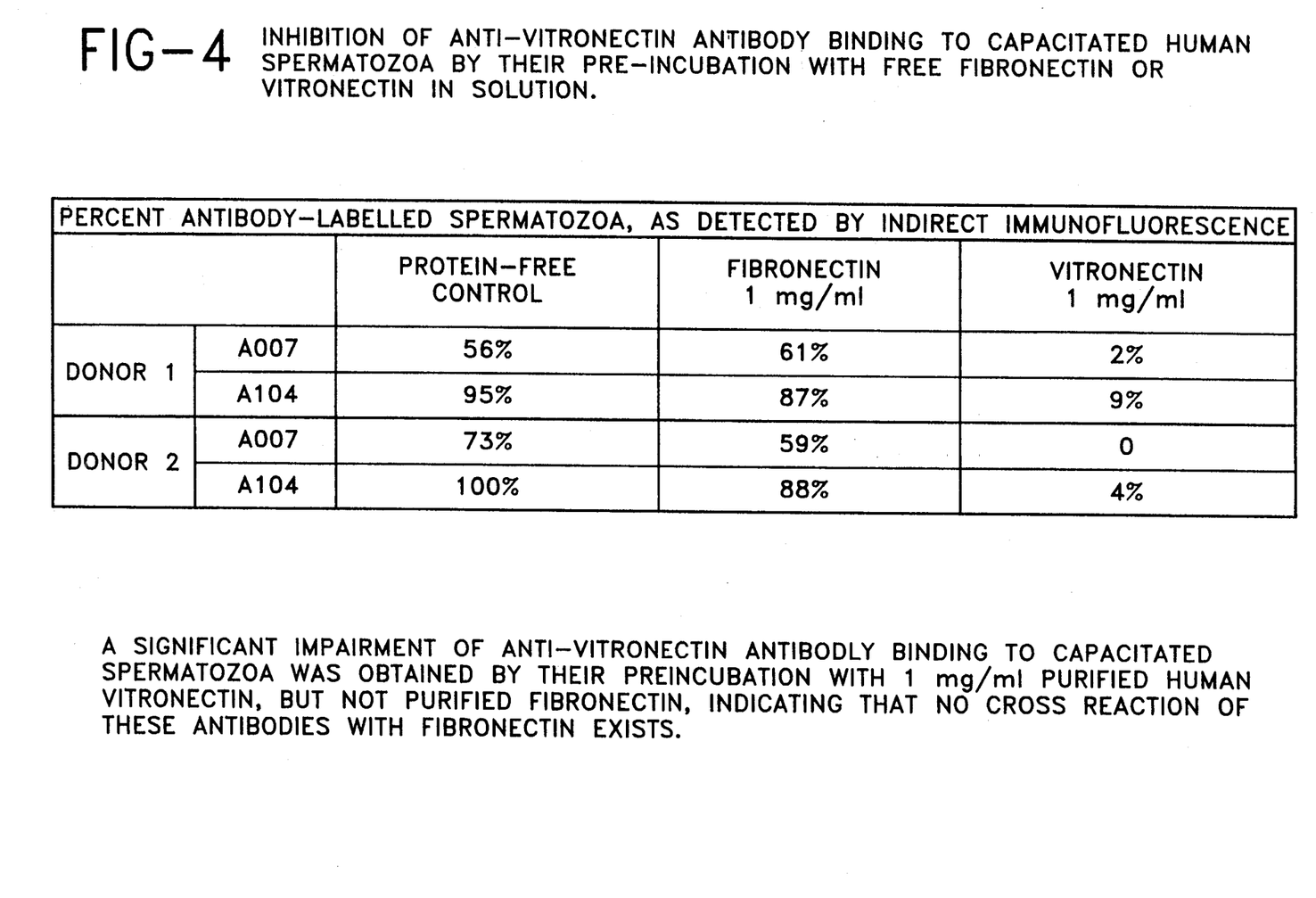
FIG. 4 illustrates inhibition of anti-vitronectin antibody binding to capacitated human spermatozoa by their pre-incubation with free fibronectin or vitronectin in solution.
Figure 5:
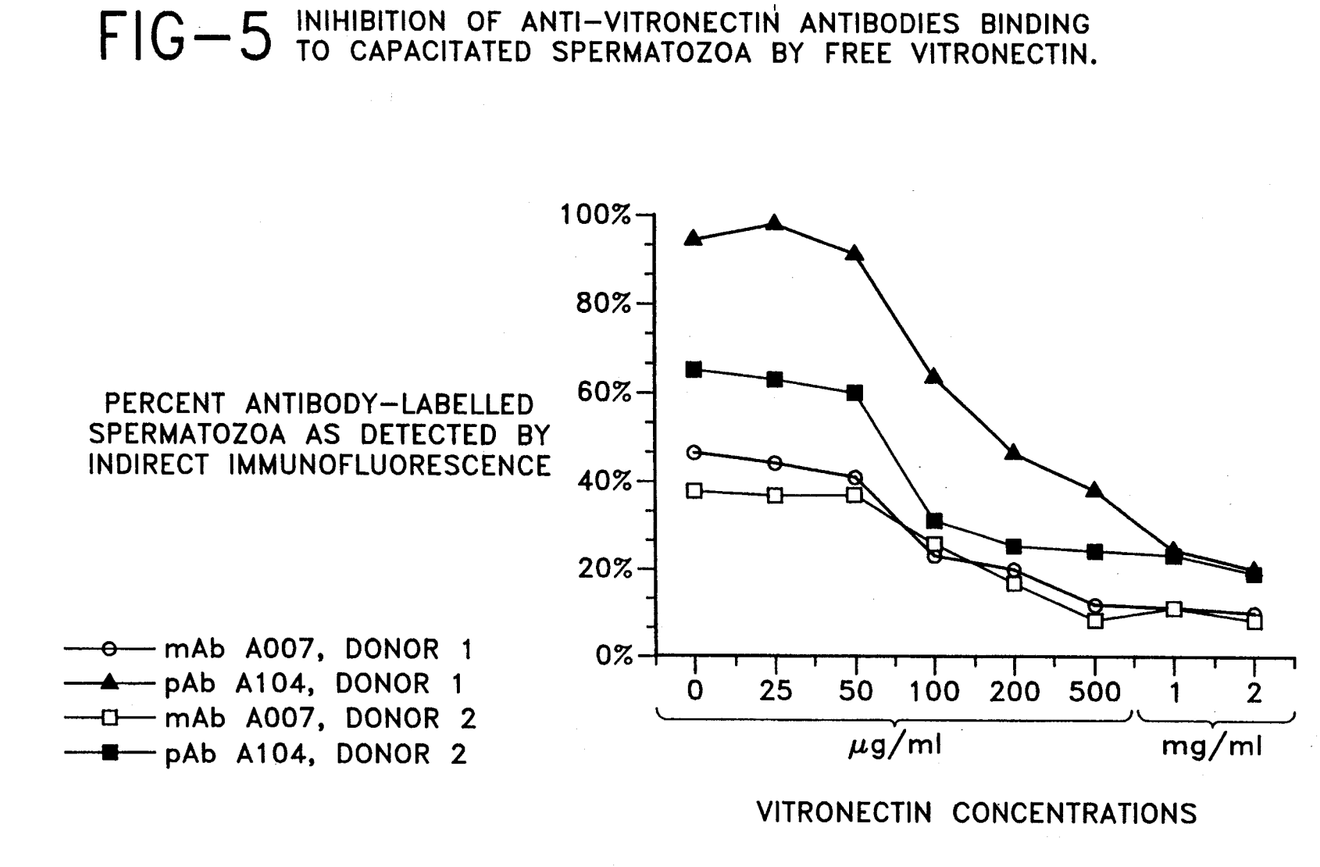
FIG. 5 illustrates inhibition of anti-vitronectin antibodies binding to capacitated spermatozoa by free vitronectin.

As vitronectin appeared to be present on the equatorial region of spermatozoa, which is the region of fusion with the oolemma, further studies were performed with anti-vitronectin antibodies in order to demonstrate the specificity of binding. An inhibition study was performed with the two anti-vitronectin antibodies by adding increasing concentrations of free vitronectin (see FIG. 2). A significant inhibition of binding was observed from the 100 µg/ml vitronectin for both antibodies, although no complete inhibition was obtained, as usually described when free antigen is coincubated and not pre-incubated with antibody prior to incubation with surface-bound antigens. In order to exclude a cross reactivity of anti-vitronectin antibodies with fibronectin, given the similarity of some epitopes of the two proteins, antibodies were pre-incubated with either fibronectin or vitronectin prior to sperm exposure (see FIG. 4). While fibronectin at a 1 mg/ml concentration did not significantly inhibit the binding of anti-vitronectin antibodies to capacitated spermatozoa, the pre-incubation of antibodies with vitronectin eliminated their reactivity with spermatozoa, suggesting that they recognize only vitronectin and not fibronectin. To exclude the possibility of binding of exogenous fibronectin or vitronectin which may have contaminated the media used for sperm washing and capacitation, a Dot-blot of the media was performed utilizing the anti-vitronectin A007 mAb and the anti-fibronectin-FN 15 mAb. No proteins reacting with these antibodies were detected, as shown in FIG. 3, indicating that fibronectin and vitronectin detected on the sperm surface are endogenous proteins and not absorbed from the medium during capacitation. In addition, no cross reactivity with fibronectin of antibodies directed against vitronectin was demonstrated, and vice versa. The Dot-blot of the sperm membrane extract, obtained by sperm solubilization with Chaps, confirmed the presence of vitronectin and fibronectin as plasma membrane proteins of capacitated spermatozoa (see FIG. 4). Fibronectin was detected as a stronger purple spot following substrate addition when compared to vitronectin, indicating a higher concentration. However, both proteins were clearly detected.

Although illustrated in terms of evaluating of sample of human sperm for lack of capacitation based upon fibronectin, vitronectin and laminin expression, the method of the present invention, as provided by the method and materials of the Examples 1-16, can readily be adapted by those skilled in the art of immunology to provide for an effective method for evaluating the sperm of other mammalian species using similar RGD-containing polypeptides.

While there have been described what are presently believed to be the preferred embodiments of the present invention disclosed herein, those skilled in the art will realize that changes and modifications may be made thereto without departing from the spirit or the scope of the invention, and it is intended to claim all such changes and modifications as fall within the true scope of the invention.

What is claimed is:

1. A method for detecting for presence of infertility in a mammalian male test subject comprising:
    (a) potentiating a sample of spermatozoa obtained from said subject by subjecting it to conditions suitable for inducing capacitation of said sample;
    (b) exposing said sample from step (a) to conditions suitable for promoting an acrosome reaction of said sample;
    (c) contacting said sample of step (b) to at least one of a polyclonal or a monoclonal antibody which specifically binds a polypeptide comprising an Arginine-Glycine-Aspartate amino acid triplet for a sufficient period of time and under conditions suitable to permit binding of said antibody with said spermatozoa, and determining the extent of antibody binding, wherein a relative increase in antibody binding is indicative of whether the spermatozoa have undergone capacitation and the acrosome reaction and wherein a lack of antibody binding is indicative of the absence of fertility.

2. A method according to claim 1, wherein said polypeptide is selected from the group consisting of a surface ligand glycoprotein, a fragment of said glycoprotein, a synthetic polypeptide having an amino acid sequence substantially corresponding to the amino acid sequence of said glycoprotein and a fragment of said synthetic polypeptide.

3. A method according to claim 2, wherein said polypeptide is of the same genus and species as said test subject.

4. A method according to claim 2, further comprising selecting said polypeptide from the group consisting of vitronectin, fibronectin and laminin.

5. The method according to claim 4, wherein said one of said polyclonal or said monoclonal antibody is selected from the group consisting of F-1509, IgG1 FN-15, A 104 and A007.

6. A method according to claim 1, further comprising the step of obtaining a semen specimen from said subject and subsequently separating and isolating spermatozoa from said semen specimen.

7. A method for detecting the inability of a sample of mammalian spermatozoa to undergo capacitation comprising:
    potentiating a sample of spermatozoa obtained from said subject by subjecting it to conditions suitable for inducing capacitation of said sample; and
    contacting said sample to at least one of a polyclonal or a monoclonal antibody which specifically binds a polypeptide comprising an Arginine-Glycine-Aspartate amino acid triplet for a sufficient period of time and under conditions suitable to permit binding of said antibody with said spermatozoa, and determining the extent of antibody binding, wherein a relative increase in antibody binding is indicative of whether the spermatozoa have undergone capacitation and wherein a lack of binding is indicative of the absence of capacitation.

8. A method according to claim 7, wherein said polypeptide is selected from the group consisting of a surface ligand glycoprotein, a fragment of said glycoprotein, a synthetic polypeptide having an amino acid sequence substantially corresponding to the amino acid sequence of said glycoprotein and a fragment of said synthetic polypeptide.

9. A method according to claim 8, wherein said polypeptide is of the same genus and species as said test subject.

10. A method according to claim 8, further comprising selecting said polypeptide from the group consisting of vitronectin, fibronectin and laminin.

11. A method according to claim 10, wherein said one of said polyclonal or said monoclonal antibody is selected from the group consisting of F-1509, IgG1 FN-15, A104 and A007.

12. A method according to claim 7, further comprising the step of obtaining a semen specimen from said subject and subsequently separating and isolating spermatozoa from said semen specimen.

* * * * *